United States Patent
Wang

(10) Patent No.: US 6,262,230 B1
(45) Date of Patent: Jul. 17, 2001

(54) ANALOGS OF THYMOSIN $\alpha_1$

(75) Inventor: Su-Sun Wang, Belmont, CA (US)

(73) Assignee: SciClone Pharmaceuticals Inc., San Mateo, CA (US)

( * ) Notice: Subject to any disclaimer, the term of this patent is extended or adjusted under 35 U.S.C. 154(b) by 0 days.

(21) Appl. No.: 08/188,232

(22) Filed: Jan. 28, 1994

(51) Int. Cl.$^7$ .................................................... C07K 7/08
(52) U.S. Cl. ........................ 530/324; 530/326; 530/334
(58) Field of Search .................................. 530/324, 326, 530/334

(56) References Cited

U.S. PATENT DOCUMENTS

| | | | |
|---|---|---|---|
| 4,079,127 | 3/1978 | Goldstein | 514/12 |
| 4,116,951 | 9/1978 | Wang | 530/324 |
| 4,148,788 | 4/1979 | Wang | 530/324 |
| 4,855,407 | 8/1989 | Wang | 530/324 |

OTHER PUBLICATIONS

Rittle et al., *Experientia*, 32(2), 246–248, 1976.*
Abiko et al., *Chem. Absts.*, 97(23): 198544z, 1982.*
Birr et al., *Chem. Absts.*, 98(7): 54448u, 1981.*
Doria et al., *Chem. Absts.*, 105(13): 109096y, 1986.*
Haritos et al, PNAS, vol. 81, pp. 1008–1011, (Feb. 1984).*
Caldarella et al, PNAS, vol. 80, pp. 7424–7427, (Dec. 1983).*
Zatz et al, Gerontology, vol. 31, pp. 263–277, (1985).*
Abiko et al, Chem. Pharm. Bull., vol. 39(3), pp. 752–756, (1991).*
Abiko et al, Chem. Pharm. Bull., vol. 33(12), pp. 5419–5427, (1985).*
Ishimura et al, Molecular Immunology, vol. 23(7), pp. 701–707, (1986).*

* cited by examiner

*Primary Examiner*—T. Wessendorf
(74) *Attorney, Agent, or Firm*—Rothwell, Figg, Ernst & Manbeck

(57) ABSTRACT

Compounds of the formula:

X-Ser-Asp-Ala-Ala-Val-Asp-Thr-Ser- (I)
Ser-Glu-Ile-Thr-Thr-Lys-Asp-Leu-Z wherein X is an acetyl or pyroglutamyl group and Z is —NH$_2$, -Lys-Glu-Lys-Lys-Glu-Val-Val-Glu-Glu-Ala-Glu-Asn-Pro-NH$_2$, -Lys-Glu-Lys-Lys-Glu-Val-Val-Glu-Glu-Ala-Glu-Asn-Gly-NH$_2$, or -Lys-Glu-Lys-Lys-Glu-Val-Val-Glu-Glu-Ala-Glu-Asn with the proviso that when X is a pyroglutamyl group, Z is -Lys-Glu-Lys-Lys-Glu-Val-Val-Glu-Glu-Ala-Glu-Asn, and when X is an acetyl group, Z is other than -Lys-Glu-Lys-Lys-Glu-Val-Val-Glu-Glu-Ala-Glu-Asn and methods for the production thereof. The compounds are thymosin $\alpha_1$-related compounds having uses including treatment of endotoxicity in animals.

7 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (v) FRAGMENT TYPE: N-terminal (ix) FEATURE:
      (A) NAME/KEY: Modified-site
      (B) LOCATION: 1
      (D) OTHER INFORMATION: /label= acetyl- (ix) FEATURE:
      (A) NAME/KEY: Modified-site (B) LOCATION: 16
            (D) OTHER INFORMATION: /label= -amide (xi) SEQUENCE DESCRIPTION: SEQ ID NO:1:

Ser Asp Ala Ala Val Asp Thr Ser Ser Glu Ile Thr Thr Lys Asp Leu
1               5                   10                  15

(2) INFORMATION FOR SEQ ID NO:2:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 1
        (D) OTHER INFORMATION: /label= acetyl- (ix) FEATURE:
        (A) NAME/KEY: Modified-site
        (B) LOCATION: 29
        (D) OTHER INFORMATION: /label= -amide (xi) SEQUENCE DESCRIPTION: SEQ ID NO:2:

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn Pro
            20                  25

(2) INFORMATION FOR SEQ ID NO:3:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Modified-site
        (B) LOCATION: 1
        (D) OTHER INFORMATION: /label= acetyl- (ix) FEATURE:
        (A) NAME/KEY: Modified-site
        (B) LOCATION: 29
        (D) OTHER INFORMATION: /label= -amide (xi) SEQUENCE DESCRIPTION: SEQ ID NO:3:

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn Gly
            20                  25

(2) INFORMATION FOR SEQ ID NO:4:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION: 1
        (D) OTHER INFORMATION: /note= "pyroglutamic acid"

(xi) SEQUENCE DESCRIPTION: SEQ ID NO:4:

Xaa Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn
            20                  25

ANALOGS OF THYMOSIN $\alpha_1$

BACKGROUND OF THE INVENTION

1. Field of the Invention

The invention involves new synthetic compounds related to thymosin $\alpha_1$ and novel methods for the synthesis thereof.

2. Description of the Prior Art

Thymosins are polypeptide immune modifiers derived from the thymus gland. Thymosins have been shown to induce T-cell differentiation and enhance immunological functions.

A partially purified extract of calf thymus, called thymosin fraction 5, contains a number of peptide products of the thymus gland, including a component referred to as thymosin $\alpha_1$.

Thymosin $\alpha_1$ was initially isolated from thymosin fraction 5, and has been sequenced and chemically synthesized (U.S. Pat. Nos. 4,079,127; 4,148,788; and 4,855,407).

The sequence of thymosin $\alpha_1$ is highly analogous in mice, calves, and humans. Thymosin $\alpha_1$ has 28 amino acids and has been shown to have activity in modulating the immune system. The immunological activity of thymosin $\alpha_1$ includes stimulation of alpha- and gamma-interferon production, increasing macrophage migration inhibitory factor production, inducing expression of T-cell markers, including interleukin-2 receptors, and improving helper T-cell activity.

There remains a need in the art for new synthetic compounds which can function like natural products of the thymus gland, are stable, and are easy to synthesize.

SUMMARY OF THE INVENTION

The present invention relates to compounds of the formula:

X-Ser-Asp-Ala-Ala-Val-Asp-Thr-Ser- (I)
Ser-Glu-Ile-Thr-Thr-Lys-Asp-Leu-Z wherein X is an acetyl or pyroglutamyl group and Z is —NH$_2$, -Lys-Glu-Lys-Lys-Glu-Val-Val-Glu-Glu-Ala-Glu-Asn-Pro-NH$_2$, -Lys-Glu-Lys-Lys-Glu-Val-Val-Glu-Glu-Ala-Glu-Asn-Gly-NH$_2$, or -Lys-Glu-Lys-Lys-Glu-Val-Val-Glu-Glu-Ala-Glu-Asn with the proviso that when X is a pyroglutamyl group, Z is -Lys-Glu-Lys-Lys-Glu-Val-Val-Glu-Glu-Ala-Glu-Asn, and when X is an acetyl group, Z is other than -Lys-Glu-Lys-Lys-Glu-Val-val-Glu-Glu-Ala-Glu-Asn and methods for the production thereof.

DETAILED DESCRIPTION OF THE PREFERRED EMBODIMENTS

The compounds of the invention are related to thymosin $\alpha_1$, and are immune system modulators that are useful in the treatment of various diseases and indications which are responsive to immune system modulators. The immune potentiating compounds of the present invention can be utilized to reconstitute immune functions in immuno-deprived and immuno-depressed patients, and can be utilized for the treatment of immuno-deficiency diseases.

One specific example of an inventive compound of the formula (I) above is thymosin $\alpha_1$-N$_{16}$ amide (SEQ ID NO:1), wherein X is an acetyl group and Z is —NH$_2$. Further examples in accordance with the present invention are thymosin $\alpha_1$-Pro amide (SEQ ID NO:2), wherein X is an acetyl group and Z is -Lys-Glu-Lys-Lys-Glu-Val-Val-Glu-Glu-Ala-Glu-Asn-Pro-NH$_2$ and thymosin $\alpha_1$-Gly amide (SEQ ID NO:3), wherein X is an acetyl group and Z is -Lys-Glu-Lys-Lys-Glu-Val-Val-Glu-Glu-Ala-Glu-Asn-Gly-NH$_2$. The invention also is applicable to pyroglutamyl-desacetyl-thymosin $\alpha_1$ (SEQ ID NO:4), wherein X is a pyroglutamyl group and Z is -Lys-Glu-Lys-Lys-Glu-Val-Val-Glu-Glu-Ala-Glu-Asn.

The invention also includes novel intermediates and precursors of compounds in accordance with formula (I) above.

Examples of intermediates and precursors include compounds of the formula:

X$_1$-Thr-Lys-Asp-Leu-NH$_2$ (II)

wherein X$_1$ is Thr, Ile-Thr, Glu-Ile-Thr, Ser-Glu-Ile-Thr, Ser-Ser-Glu-Ile-Thr, Thr-Ser-Ser-Glu-Ile-Thr, Asp-Thr-Ser-Ser-Glu-Ile-Thr, Val-Asp-Thr-Ser-Ser-Glu-Ile-Thr, Ala-Val-Asp-Thr-Ser-Ser-Glu-Ile-Thr, Ala-Ala-Val-Asp-Thr-Ser-Ser-Glu-Ile-Thr, Asp-Ala-Ala-Val-Asp-Thr-Ser-Ser-Glu-Ile-Thr, or Ser-Asp-Ala-Ala-Val-Asp-Thr-Ser-Ser-Glu-Ile-Thr, compounds of the formula:

X$_2$-Ala-Glu-Asn-Pro-NH$_2$ (III)

wherein X$_2$ is Glu, Glu-Glu, Val-Glu-Glu, Val-Val-Glu-Glu, Glu-Val-Val-Glu-Glu, Lys-Glu-Val-Val-Glu-Glu, Lys-Lys-Glu-Val-Val-Glu-Glu, Glu-Lys-Lys-Glu-Val-Val-Glu-Glu, Lys-Glu-Lys-Lys-Glu-Val-Val-Glu-Glu, Leu-Lys-Glu-Lys-Lys-Glu-Val-Val-Glu-Glu, Asp-Leu-Lys-Glu-Lys-Lys-Glu-Val-Val-Glu-Glu, Lys-Asp-Leu-Lys-Glu-Lys-Lys-Glu-Val-Val-Glu-Glu, Thr-Lys-Asp-Leu-Lys-Glu-Lys-Lys-Glu-Val-Val-Glu-Glu, Thr-Thr-Lys-Asp-Leu-Lys-Glu-Lys-Lys-Glu-Val-Val-Glu-Glu, Ile-Thr-Thr-Lys-Asp-Leu-Lys-Glu-Lys-Lys-Glu-Val-Val-Glu-Glu, Glu-Ile-Thr-Thr-Lys-Asp- Leu-Lys-Glu-Lys-Lys-Glu-Val-Val-Glu-Glu, Ser-Glu-Ile-Thr-Thr-Lys-Asp-Leu-Lys-Glu-Lys-Lys-Glu-Val-Val-Glu-Glu, Ser-Ser-Glu-Ile-Thr-Thr-Lys-Asp-Leu-Lys-Glu-Lys-Lys-Glu-Val-Val-Glu-Glu, Thr-Ser-Ser-Glu-Ile-Thr-Thr-Lys-Asp-Leu-Lys-Glu-Lys-Lys-Glu-Val-Val-Glu-Glu, Asp-Thr-Ser-Ser-Glu-Ile-Thr-Thr-Lys-Asp-Leu-Lys-Glu-Lys-Lys-Glu-Val-Val-Glu-Glu, Val-Asp-Thr-Ser-Ser-Glu-Ile-Thr-Thr-Lys-Asp-Leu-Lys-Glu-Lys-Lys-Glu-Val-Val-Glu-Glu, Ala-Val-Asp-Thr-Ser-Ser-Glu-Ile-Thr-Thr-Lys-Asp-Leu-Lys-Glu-Lys-Lys-Glu-Val-Val-Glu-Glu, Ala-Ala-Val-Asp-Thr-Ser-Ser-Glu-Ile-Thr-Thr-Lys-Asp-Leu-Lys-Glu-Lys-Lys-Glu-Val-Val-Glu-Glu, Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu, or Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu, and compounds of the formula:

X$_3$-Ala-Glu-Asn-Gly-NH$_2$ (IV)

wherein X$_3$ is Glu, Glu-Glu, Val-Glu-Glu, Val-Val-Glu-Glu, Glu-Val-Val-Glu-Glu, Lys-Glu-Val-Val-Glu-Glu, Lys-Lys-Glu-Val-Val-Glu-Glu, Glu-Lys-Lys-Glu-Val-Val-Glu-Glu, Lys-Glu-Lys-Lys-Glu-Val-Val-Glu-Glu, Leu-Lys-Glu-Lys-Lys-Glu-Val-Val-Glu-Glu, Asp-Leu-Lys-Glu-Lys-Lys-Glu-Val-Val-Glu-Glu, Lys-Asp-Leu-Lys-Glu-Lys-Lys-Glu-Val-Val-Glu-Glu, Thr-Lys-Asp-Leu-Lys-Glu-Lys-Lys-Glu-Val-Val-Glu-Glu, Thr-Thr-Lys-Asp-Leu-Lys-Glu-Lys-Lys-Glu-Val-Val-Glu-Glu, Ile-Thr-Thr-Lys-Asp-Leu-Lys-Glu-Lys-Lys-Glu-Val-Val-Glu-Glu, Glu-Ile-Thr-Thr-Lys-Asp-Leu-Lys-Glu-Lys-Lys-Glu-Val-Val-Glu-Glu, Ser-Glu-Ile-Thr-Thr-Lys-Asp-Leu-Lys-Glu-Lys-Lys-Glu-Val-Val-Glu-Glu, Ser-Ser-Glu-Ile-Thr-Thr-Lys-Asp-Leu-Lys-Glu-Lys-Lys-Glu-Val-Val-Glu-Glu, Thr-Ser-Ser-Glu-Ile-Thr-Thr-Lys-Asp-Leu-Lys-Glu-Lys-Lys-Glu-Val-Val-Glu-Glu, Asp-Thr-Ser-Ser-Glu-Ile-Thr-Thr-Lys-Asp-Leu-Lys-Glu-Lys-Lys-Glu-Val-Val-Glu- Glu, Ala-Val-Asp-Thr-Ser-Ser-Glu-Ile-Thr-Thr-Lys-Asp-Leu-Lys-Glu-Lys-Lys-Glu-Val-Val-Glu-Glu, Ala-Ala-Val-Asp-Thr-Ser-Ser-Glu-Ile-Thr-Thr-Lys-Asp-Leu-Lys-Glu-Lys-Lys-Glu-Val-Val-Glu-Glu, Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu, or Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu.

Compounds of formulas III and IV can be described as:

$X_2$-Ala-Glu-Asn-Y (IVa)

wherein Y is Pro-NH$_2$ or Gly-NH$_2$, and $X_2$ is as defined above for formula (III).

The compounds, intermediates, and precursors of the present invention, collectively referred to herein as thymosin peptides, and including analogs and derivatives of thymosin $\alpha_1$, can be provided by any suitable method of peptide synthesis. The compounds are preferably synthesized by solid phase peptide synthesis and most preferably by solid phase synthesis on 4-methylbenzhydrylamine resin.

Cleavage of the peptide from the resin can be achieved by any suitable method, for example, by acidolysis. Acids such as hydrofluoric acid and trifluoromethane sulfonic acid (CF$_3$SO$_3$H) are suitable. Most preferably, the acid used is trifluoromethane sulfonic acid. Preferably, protected peptide resin is mixed with at solution of anisole (about 5% to about 25%) and thioanisole (about 5% to about 25%) in trifluoroacetic acid, and acidolysis is achieved by treatment with about 5% to about 10% trifluoromethane sulfonic acid (CF$_3$SO$_3$H). Most preferably, trifluoromethane sulfonic acid is used as a 50% solution in trifluoroacetic acid in approximately equal proportion to the amount of peptide resin to be cleaved.

The invention is further illustrated by the following examples, which are not intended to be limiting.

EXAMPLES

Example 1
Ac-Ser-Asp-Ala-Ala-Val-Asp-Thr-Ser-Ser-Glu-Ile-Thr-Thr-Lys-Asp-Leu-NH$_2$ Thymosin $\alpha_1$-N$_{16}$ Amide 4-Methylbenzhydrylamine Resin (2.01 g; 0.55 mmol/g) was placed in a peptide synthesis flask and washed with 40 mL of dichloromethane 3 times. The resin was then neutralized with 40 mL of 10% triethylamine for 1 minute and again for 10 minutes, then washed 3 times with dichloromethane. The neutralized resin showed a strong positive reaction to the ninhydrin test. It was then coupled with 3.0 mmol of t-Butyloxycarbonyl-L-Leucine (Boc-Leu, 0.784 g) in the presence of 3.0 mmol of N,N'-dicyclohexylcarbodiimide (DCC, 0.618 g) in dichloromethane for 150 minutes. The synthesis was continued by performing the solid phase synthesis procedure as indicated below. [Steps 1 to 11 represent all the manipulations required of a synthetic cycle wherein one amino acid residue is incorporated into the growing peptide chain attached to the resin]:

1) prewash with 50% trifluoroacetic acid in dichlormethane,
2) stir in 50% trifluoroacetic acid for 30 minutes,
3) wash 3 times with dichloromethane,
4) prewash with 10% triethylamine in dichloromethane,
5) stir in 10% triethylamine for 3 minutes,
6) wash 3 times with dichloromethane,
7) test resin for ninhydrin reaction (should be strongly positive),
8) stir the resin with 0.970 g of Boc-Asp(OBzl) (3.0 mmol) and 0.618 g of DCC (3.0 mmol) in dichloromethane for 120 minutes,
9) wash 2 times with 50% isopropanol in dichloromethane,
10) wash 3 times with dichloromethane,
11) test for ninhydrin reaction. If negative, go to next synthetic cycle. If positive, repeat steps 8 to 11.

The solid phase peptide synthesis cycle was repeated with the following amino acid derivatives, in step 8 of each cycle, sequentially, one at a time in that order, until the desired amino acid sequence was constructed: Boc-Lys(ClZ), (1.244 g); Boc-Thr(Bzl), (0.928 g); Boc-Thr(Bzl), (0.928 g); Boc-Ile, (0.720 g); Boc-Glu(OBzl), (1.01 g); Boc-Ser(Bzl), (0.886 g); Boc-Ser(Bzl) (0.886 g); Boc-Thr(Bzl), (0.928 g); Boc-Asp(OBzl), (0.970 g); Boc-Val, (0.652 g); Boc-Ala, (0.568 g), Boc-Ala, (0.568 g); Boc-Asp(OBzl), (0.970 g); Boc-Ser(Bzl), (0.886 g), and Acetic Acid (0.180 g). The resultant protected acetyl-hexadecapeptide resin, Ac-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(ClZ)-Asp(OBzl)-Leu-MBHA-Resin, thus obtained weighed 4.25 g.

Part of this protected hexadecapeptide resin (1.08 g) was mixed with 2 mL of anisole and stirred with 10 mL liquid HF for 45 minutes at 0°. The excess acid was removed by evaporation at 0° in vacuo, and the residue washed with ether. The peptide material was extracted into 50 mL of 2% ammonium acetate and desalted on a Sephadex G-10 column (0.1 M acetic acid). Lyophilization of the peptide peak provided 0.204 g of crude peptide amide.

A portion of the crude peptide (100 mg) was purified on a Hamilton PRP-1 column (2.15×25 cm, 10$\mu$) and eluted with a buffered solvent of 53.5 g/L isopropanol in 0.035 M potassium phosphate, pH 5 (flow rate=5 mL/minute; monitored at 227 nm). The fractions containing pure peptide were pooled, desalted on a Sephadex G-10 column and lyophilized to yield 26 mg thymosin $\alpha_1$-N$_{16}$ amide. The material was found to be homogeneous on high performance capillary electrophoresis. Amino Acid Analysis: Asp, 3.00 (3); Thr, 2.68 (3); Ser, 2.67 (3); Glu, 1.04 (1); Ala, 1.88 (2); Val, 0.97 (1); Ile, 1.01 (1); Leu, 1.02 (1); Lys, 1.00 (1). Mass spectrometric analysis showed that the compound had the expected molecular weight; MH$^+$=1,693.8, MNa$^+$=1,716.9 (Calculated MW=1,693.8).

Example 2
Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-Pro-NH$_2$ Thymosin $\alpha_1$-Pro Amide 4-Methylbenzhydrylamine Resin (1.0 g; 0.55 mmol/g) was placed in a peptide synthesis flask and washed with 20 mL of dichloromethane 3 times. The resin was then neutralized with 10% triethylamine for 1 minute and again for 10 minutes, then washed three times with dichloromethane. The neutralized resin showed a strong positive reaction to the ninhydrin test. It was then coupled with 1.5 mmol of Boc-Pro (0.322 g) in the presence of 1.5 mmol DCC (0.309g) in dichloromethane for 120 minutes. The synthesis was continued by performing solid phase peptide synthesis cycles as outlined in Example 1, with the following amino acid derivatives in step 8 of each cycle, sequentially, one at a time in that order, until the desired peptide sequence was constructed on the resin: Boc-Asn, (0.348 g with addition of 0.405 g HOBT in dimethylformamide), Boc-Glu(OBzl) (0.506 g); Boc-Ala, (0.284 g), Boc-Glu(OBzl) (0.506 g), Boc-Glu(OBzl) (0.506 g), Boc-Val (0.326 g), Boc-Val (0.326 g), Boc-Glu(OBzl) (0.506 g), Boc-Lys(ClZ) (0.622 g), Boc-Lys (ClZ) (0.622 g), Boc-Glu(OBzl) (0.506 g), Boc-Lys(ClZ) (0.622 g), Boc-Leu (0.374 g), Boc-Asp(OBzl) (0.486 g), Boc-Lys(ClZ) (0.602 g); Boc-Thr(Bzl) (0.464 g), Boc-Thr(Bzl) (0.464 g), Boc-Ile (0.360 g), Boc-Glu(OBzl) (0.506 g), Boc-Ser(Bzl) (0.443 g), Boc-Ser (Bzl) (0.443 g), Boc-Thr(Bzl) (0.464 g), Boc-Asp(OBzl) (0.485 g), Boc-Val (0.326 g), Boc-Ala (0.284 g), Boc-Ala (0.284 g), Boc-Asp (OBzl) (0.485 g), Boc-Ser(Bzl) (0.443 g) and Acetic Acid (0.090 g). The resultant protected acetyl-nonacosapeptide resin, Ac-Ser(Bzl)-Asp(OBzl)-Ala-Ala-Val-Asp(OBzl)-Thr (Bzl)-Ser(Bzl)-Ser(Bzl)-Glu(OBzl)-Ile-Thr(Bzl)-Thr(Bzl)- Lys(ClZ)-Asp(OBzl)-Leu-Lys(ClZ-Glu(OBzl)-Lys(ClZ)- Lys(ClZ)-Glu(OBzl)-Val-Val-Glu(OBzl)-Glu(OBzl)-Ala- Glu(OBzl)-Asn-Pro-MBHA-Resin, thus obtained weighed 2.89 g.

A portion of the above protected peptide resin (0.995 g) was cleaved, and treated as described in Example 1 to give 0.335 g of crude thymosin $\alpha_1$-Pro-NH$_2$. It was purified on a Hamilton PRP-1 column as described in Example 1 to yield 51 mg of Thymosin $\alpha_1$-Pro Amide. The material was found to be homogeneous on analytical high performance liquid chromatography and capillary electrophoresis. Amino Acid Analysis: 24 hr hydrolysis; Asp, 4.00 (4); Thr, 3.06 (3); Ser, 2.85 (3); Glu, 6.06 (6); Pro, 1.12 (1); Ala, 2.94 (3); Val, 1.88 (3); Ile, 0.98 (1); Leu, 1.00 (1); Lys, 3.98 (4). 100 hr hydrolysis; Asp, 4.00 (4); Thr, 2.69 (3); Ser, 2.12 (3); Glu, 6.17 (6); Pro, 1.04 (1); Ala, 3.01 (3); Val, 2.96 (3); Ile, 1.08 (1); Leu, 1.08 (1); Lys, 4.12 (4). Mass spectrometric analysis showed that the peptide had the expected molecular weight; MH$^+$=3,205.1 (Calculated MW=3,204.5).

Example 3
Ac-Ser-Asp-Ala-Ala-Val-Asp-Thr-Ser-Ser-Glu-Ile-Thr- Thr-Lys-Asp-Leu-Lys-Glu-Lys-Lys-Glu-Val-Val-Glu-Glu- Ala-Glu-Asn-Gly-NH$_2$ Thymosin $\alpha_1$-Gly Amide 4-Methylbenzhydrylamine Resin (1.0 g; 0.55 mmol/g) was placed in a peptide synthesis flask and washed with 20 mL of dichloromethane 3 times. The resin was then neutralized with 10% triethylamine for 1 minute and again for 10 minutes, then washed 3 times with dichloromethane. The neutralized resin showed a strong positive reaction to the ninhydrin test. It was coupled with 1.5 mmol of Boc-Gly (0.263 g) in the presence of 1.5 mmol DCC (0.309 g) in dichloromethane for 120 minutes. The synthesis was continued by performing solid phase peptide synthesis cycles as outlined in Example 1, with the following amino acid derivatives used in step 8 of each cycle, sequentially, one at a time in that order, until the desired peptide was assembled on the resin: Boc-Asn, (0.348 g with addition of 0.405 g HOBT in dimethylformamide), Boc-Glu(OBzl) (0.506 g); Boc-Ala, (0.284 g), Boc-Glu(OBzl) (0.506 g), Boc-Glu (OBzl) (0.506 g), Boc-Val (0.326 g), Boc-Val (0.326 g), Boc-Glu(OBzl) (0.506 g), Boc-Lys(ClZ) (0.622 g), Boc-Lys (ClZ) (0.622 g), Boc-Glu(OBzl) (0.506 g), Boc-Lys(ClZ) (0.622 g), Boc-Leu (0.374 g), Boc-Asp(OBzl) (0.485 g), Boc-Lys(ClZ) (0.622 g); Boc-Thr(Bzl) (0.464 g), Boc-Thr (Bzl) (0.464 g), Boc-Ile (0.360 g), Boc-Glu(OBzl) (0.506 g), Boc-Ser(Bzl) (0.443 g), Boc-Ser (Bzl) (0.443 g), Boc-Thr (Bzl) (0.464 g), Boc-Asp(OBzl) (0.485 g), Boc-Val (0.326 g), Boc-Ala (0.284 g), Boc-Ala (0.284 g), Boc-Asp(OBzl) (0.485 g), Boc-Ser(Bzl) (0.443 g) and Acetic Acid (0.090 g). The resultant protected acetyl-nonacosapeptide resin, Ac-Ser(Bzl)-Asp(OBzl)-Ala-Ala-Val-Asp(OBzl)-Thr(Bzl)- Ser(Bzl)-Ser(Bzl)-Glu(OBzl)-Ile-Thr(Bzl)-Thr(Bzl)- Lys(ClZ)-Asp(OBzl)-Leu-Lys(ClZ)-Glu(OBzl)-Lys(ClZ)-Lys (ClZ)-Glu(OBzl)-Val-Val-Glu(OBzl)-Glu(OBzl)-Ala-Glu (OBzl)-Asn-Gly-MBHA Resin, thus obtained weighed 2.70 g.

Part of the above protected peptide resin (0.996 g) was mixed with 2 mL anisole, 2 mL thioanisole and 6 mL trifluoroacetic acid. While stirring, 1.1 mL 50% CF$_3$SO$_3$H in trifluoroacetic acid was added and the stirring continued for 35 minutes. The mixture was then poured into 100 mL ether. The gummy precipitate thus formed was washed briefly with more fresh ether. The peptide material was then extracted into 50 mL of 30% ammonium acetate followed by 20 mL water. The combined extracts were evaporated to a smaller volume, desalted on a Sephadex G-10 column (2.6×85 cm, 0.1 M acetic acid) and lyophilized to provide 0.323 g of crude nonacosapeptide.

A portion of this crude peptide (0.161 g) was purified on a Hamilton PRP-1 column as described in Example 1 to yield 40.2 mg thymosin $\alpha_1$-Gly Amide. The material was found to be homogeneous on analytical high performance liquid chromatography. Amino Acid Analysis: 24 hr hydrolysis; Asp, 4.00 (4); Thr, 2.96 (3); Ser, 2.75 (3); Glu, 5.97 (6); Gly, 1.03 (1)l Ala, 2.96 (3); Val, 1.84 (3); Ile, 1.05 (1); Leu, 1.04 (1); Lys, 3.96 (4). 100 hr hydrolysis; Asp, 4.00 (4); Thr, 3.00 (3); Ser, 2.41 (3); Glu, 6.18 (6); Gly, 1.03 (1); Ala, 2.87 (3); Val, 2.82 (3); Ile, 1.06 (1); Leu, 1.05 (1); Lys, 3.79 (4). Mass spectrometric analysis showed that the peptide had the expected molecular weight; MH$^+$=3,165.5 (Calculated MW=3,164.4).

Example 4
Glp-Ser-Asp-Ala-Ala-Val-Asp-Thr-Ser-Ser-Glu-Ile-Thr- Thr-Lys-Asp-Leu-Lys-Glu-Lys-Lys-Glu-Val-Val-Glu-Glu- Ala-Glu-Asn Pyroglutamyl-desacetyl thymosin $\alpha_1$ 4-methylbenzhydrylamine resin (1.0 g; 0.55 mmol/g) was placed in a peptide synthesis flask and washed with 20 mL dichloromethane 3 times. The resin was neutralized with 10% triethylamine for 1 minute and again for 10 minutes, then washed 3 times with dichloromethane. The neutralized resin showed a strong positive reaction to the ninhydrin test. It was then coupled with 1.5 mmol t-butyloxycarbonyl-L-aspartic acid β-benzyl ester (0.485 g) in the presence of 1.5 mmol DCC (0.309 g) for 60 minutes. The coupling reaction was repeated once in order to bring the resin negative to ninhydrin test. The synthesis was continued by performing solid phase peptide synthesis cycles as outlined in Example 1, with the following amino acid derivatives used in step 8 of each cycle, sequentially, one at a time in that order, until the desired peptide was assembled on the resin: Boc-Glu (OBzl) (0.506 g), Boc-Ala (0.284 g), Boc-Glu(OBzl) (0.506 g), Boc-Glu(OBzl) (0.506 g), Boc-Val (0.326 g), Boc-Val (0.326 g), Boc-Glu(OBzl) (0.506 g), Boc-Lys(ClZ) (0.622 g), Boc-Lys(ClZ) (0.622 g), Boc-Glu(OBzl) (0.506g), Boc-Lys(ClZ) (0.622g), Boc-Leu (0.374 g), Boc-Asp(OBzl) (0.485g), Boc-Lys(ClZ) (0.622 g), Boc-Thr(Bzl) (0.464 g), Boc-Thr(Bzl) (0.464 g), Boc-Ile (0.360 g), Boc-Glu(OBzl) (0.506 g), Boc-Ser(Bzl) (0.443 g), Boc-Ser(Bzl (0.443 g), Boc-Thr(Bzl) (0.464 g), Boc-Asp(OBzl) (0.485 g), Boc-Val (0.326 g), Boc-Ala (0.284 g), Boc-Ala (0.284 g), Boc-Asp (OBzl) (0.485 g), Boc-Ser(Bzl) (0.443 g) and benzyloxycarbonyl-L-pyroglutamic acid (Z-Glp) (0.395 g). The resultant protected nonacosapeptide resin, Z-Glp-Ser(Bzl)-Asp(OBzl)-Ala-Ala-Val-Asp(OBzl)-Thr(Bzl)-Ser(Bzl)-Ser(Bzl)-Glu(OBzl)-Ile-Thr(Bzl)-Thr(Bzl)-Lys(ClZ)-Asp(OBzl)-Leu-Lys(ClZ)-Glu(OBzl)-Lys(ClZ)-Lys(ClZ)-Glu(OBzl)-Val-Val-Glu(OBzl)-Glu(OBzl)-Ala-Glu(OBzl)-Asp(MBHA-Resin)-OBzl, thus obtained weighed 2.67 g.

Part of the above protected peptide resin (0.995 g) was mixed with 2 mL anisole, 2.2 mL thioanisole and 6 mL trifluoroacetic acid. While stirring, 1.1 mL of 50% $CF_3SO_3H$ in trifluoroacetic acid was added and the stirring continued for 35 minutes. The mixture was then poured into 100 mL ether. The gummy precipitate thus formed was washed briefly with more fresh ether. The peptide material was then extracted into 50 mL of 4% ammonium acetate and desalted on a Sephadex G-10 column (2.6×85 cm, 0.1 M acetic acid) and lyophilized to provide 0.229 g of crude nonacosapeptide.

A portion of this crude peptide (0.150 g) was purified on Hamilton PRP-1 column as described in Example 1 to yield 46.2 mg pyroglutamyl-desacetyl thymosin $\alpha_1$. The material was found to be homogeneous on analytical high performance liquid chromatography. Amino Acid Analysis: 24 hr hydrolysis; Asp, 4.00 (4); Thr, 3.04 (3); Ser, 2.69 (3); Glu, 6.92 (7); Ala, 2.90 (3); Val, 1.80 (3); Ile, 1.00 (1); Leu, 1.00 (1); Lys, 3.90 (4). 100 hr hydrolysis; Asp, 4.00 (4); Thr, 3.09 (3); Ser, 2.67 (3); Glu, 7.50 (7); Ala, 3.14 (3); Val, 2.83 (3); Ile, 1.04 (1); Leu, 1.08 (1); Lys, 4.05 (4). Mass spectrometric analysis showed that the peptide had the expected molecular weight; $MH^+=3,177.1$; $MNa^+=3,200.2$ (Calculated MW=3,177.4).

Example 5

Swiss-Webster mice were treated in five groups: endotoxic mice (mice injected with lipopolysaccharide endotoxin from *E. coli* at 60 mg/kg) which were otherwise untreated, and endotoxic mice treated with 3 injections of 100 μg Thymosin $\alpha_1$-$N_{16}$ Amide ($T\alpha_1$-$N_{16}$-$NH_2$) treated in two groups, Pyroglutamyl-desacetyl Thymosin $\alpha_1$ ([glp]-$T\alpha_1$), or Thymosin $\alpha_1$-Gly Amide ($T\alpha_1$-gly-$NH_2$) at 5 minutes, 2 and 4 hours post administration of the endotoxin.

The results are presented in the Table below. As can be seen, $T\alpha_1$ and its analogs, administered 3 times post administration of endotoxin, increased the survival rate of mice injected with endotoxin.

TABLE

| | Number of Mice Alive Following Lethal Endotoxin Dose | | | | | |
|---|---|---|---|---|---|---|
| | 0 hr | 24 hr | 48 hr | 72 hr | 4 days | 5 days |
| Endotoxin 60 mg/kg | 10 | 4 | 3 | 3 | 3 | 3 |
| Endotoxin 60 mg/kg plus $T\alpha_1$-$N_{16}$—$NH_2$ | 10 | 5 | 4 | 4 | 4 | 4 |
| Endotoxin 60 mg/kg plus $T\alpha_1$-$N_{16}$—$NH_2$ 100 μg 3× | 10 | 8 | 8 | 7 | 7 | 7 |
| Endotoxin 60 mg/kg plus [Glp]-$T\alpha_1$ | 8 | 8 | 8 | 8 | 8 | 8 |
| Endotoxin 60 mg/kg plus $T\alpha_1$-Gly-$NH_2$ | 8 | 8 | 8 | 8 | 8 | 8 |

What is claimed is:

1. A compound of the formula:

X-Ser-Asp-Ala-Ala-Val-Asp-Thr-Ser-  (I)

Ser-Glu-Ile-Thr-Thr-Lys-Asp-Leu-Z wherein X is an acetyl or pyroglutamyl group and Z is —NH₂, -Lys-Glu-Lys-Lys-Glu-Val-Val-Glu-Glu-Ala-Glu-Asn-Pro-NH₂, -Lys-Glu-Lys-Lys-Glu-Val-Val-Glu-Glu-Ala-Glu-Asn-Gly-NH₂, or -Lys-Glu-Lys-Lys-Glu-Val-Val-Glu-Glu-Ala-Glu-Asn with the proviso that when X is a pyroglutamyl group, Z is -Lys-Glu-Lys-Lys-Glu-Val-Val-Glu-Glu-Ala-Glu-Asn, and when X is an acetyl group, Z is other than -Lys-Glu-Lys-Lys-Glu-Val-Val-Glu-Glu-Ala-Glu-Asn.

2. The compound of claim 1 wherein X is an acetyl group and Z is —NH₂ (SEQ ID NO:1).

3. The compound of claim 1 wherein X is an acetyl group and Z is -Lys-Glu-Lys-Lys-Glu-Val-Val-Glu-Glu-Ala-Glu-Asn-Pro-NH₂ (SEQ ID NO:2).

4. The compound of claim 1 wherein X is an acetyl group and Z is -Lys-Glu-Lys-Lys-Glu-Val-Val-Glu-Glu-Ala-Glu-Asn-Gly-NH₂ (SEQ ID NO:3).

5. The compound of claim 1 wherein X is a pyroglutamyl group and Z is -Lys-Glu-Lys-Lys-Glu-Val-Val-Glu-Glu-Ala-Glu-Asn (SEQ ID NO:4).

6. A compound of the formula:

X₁-Lys-Asp-Leu-NH₂  (II)

wherein X₁ is Thr, Ile-Thr, Glu-Ile-Thr, Ser-Glu-Ile-Thr, Ser-Ser-Glu-Ile-Thr, Thr-Ser-Ser-Glu-Ile-Thr, Asp-Thr-Ser-Ser-Glu-Ile-Thr, Val-Asp-Thr-Ser-Ser-Glu-Ile-Thr, Ala-Val-Asp-Thr-Ser-Ser-Glu-Ile-Thr, Ala-Ala-Val-Asp-Thr-Ser-Ser-Glu-Ile-Thr, Asp-Ala-Ala-Val-Asp-Thr-Ser-Ser-Glu-Ile-Thr, Ser-Asp-Ala-Ala-Val-Asp-Thr-Ser-Ser-Glu-Ile-Thr, or Ac-Ser-Asp-Ala-Aila-Val-Asp-Thr-Ser-Ser-Glu-Ile-Thr, wherein Ac is an acetyl group.

7. A compound of the formula:

X₂-Ala-Glu-Asn-Y  (III)

wherein Y is Pro-NH₂ or Gly-NH₂, and X₂ is Glu, Glu-Glu, Val-Glu-Glu, Val-Val-Glu-Glu, Glu-Val-Val-Glu-Glu, Lys-Lys-Glu-Val-Val-Glu-Glu, Glu-Lys-Lys-Glu-Val-Val-Glu-Glu, Lys-Glu-Lys-Lys-Glu-Val-Val-Glu-Glu, Leu-Lys-Glu-Lys-Lys-Glu-Val-Val-Glu-Glu, Asp-Leu-Lys-Glu-Lys-Lys-Glu-Val-Val-Glu-Glu, Lys-Asp-Leu-Lys-Glu-Lys-Lys-Glu-Val-Val-Glu-Glu, Thr-Lys-Asp-Leu-Lys-Glu-Lys-Lys-Glu-Val-Val-Glu-Glu, Thr-Thr-Lys-Asp-Leu-Lys-Glu-Lys-Lys-Glu-Val-Val-Glu-Glu, Ile-Thr-Thr-Lys-Asp-Leu-Lys-Glu-Lys-Lys-Glu-Val-Val-Glu-Glu, Glu-Ile-Thr-Thr-Lys-Asp-Leu-Lys-Glu-Lys-Lys-Glu-Val-Val-Glu-Glu, Ser-Glu-Ile-Thr-Thr-Lys-Asp-Leu-Lys-Glu-Lys-Lys-Glu-Val-Val-Glu-Glu, Ser-Ser-Glu-Ile-Thr-Thr-Lys-Asp-Leu-Lys-Glu-Lys-Lys-Glu-Val-Val-Glu-Glu, Thr-Ser-Ser-Glu-Ile-Thr-Thr-Lys-Asp-Leu-Lys-Glu-Lys-Lys-Glu-Val-Val-Glu-Glu, Asp-Thr-Ser-Ser-Glu-Ile-Thr-Thr-Lys-Asp-Leu-Lys-Glu-Lys-Lys-Glu-Val-Val-Glu-Glu, Val-Asp-Thr-Ser-Ser-Glu-Ile-Thr-Thr-Lys-Asp-Leu-Lys-Glu-Lys-Lys-Glu-Val-Val-Glu-Glu, Ala-Val-Asp-Thr-Ser-Ser-Glu-Ile-Thr-Thr-Lys-Asp-Leu-Lys-Glu-Lys-Lys-Glu-Val-Val-Glu-Glu, Ala-Ala-Val-Asp-Thr-Ser-Ser-Glu-Ile-Thr-Thr-Lys-Asp-Leu-Lys-Glu-Lys-Lys-Glu-Val-Val-Glu-Glu, Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu, Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu, or Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu, wherein Ac is an acetyl group.

* * * * *

UNITED STATES PATENT AND TRADEMARK OFFICE
CERTIFICATE OF CORRECTION

PATENT NO.         : 6,262,230 B1
APPLICATION NO. : 08/188232
DATED              : July 17, 2001
INVENTOR(S)        : Su-Sun Wang It is certified that error appears in the above-identified patent and that said Letters Patent is hereby corrected as shown below:

Column 11, line 46, delete "Thr,"
Column 12, line 24, delete "Lys-Glu-Val-Val-Glu-Glu,"

Signed and Sealed this

Twenty-seventh Day of May, 2008

JON W. DUDAS
*Director of the United States Patent and Trademark Office*